United States Patent [19]

Ikeda et al.

[11] Patent Number: 5,607,948
[45] Date of Patent: Mar. 4, 1997

[54] DIPIPERIDINE DERIVATIVES

[75] Inventors: Yoshiharu Ikeda; Yasuyuki Ueki, both of Hyogo-ken; Toshio Nishihara, Osaka; Yumiko Kamikawa, Toyonaka, all of Japan

[73] Assignee: Sumitomo Pharmaceuticals Co., Ltd., Osaka-fu, Japan

[21] Appl. No.: 578,697

[22] PCT Filed: Jun. 6, 1994

[86] PCT No.: PCT/JP94/00908

§ 371 Date: Dec. 28, 1995

§ 102(e) Date: Dec. 28, 1995

[87] PCT Pub. No.: WO95/01336

PCT Pub. Date: Jan. 12, 1995

[30] Foreign Application Priority Data

Jun. 30, 1993 [JP] Japan .................... 5-189120

[51] Int. Cl.⁶ ............. A61K 31/445; C07D 211/16
[52] U.S. Cl. ............................... 514/316; 546/187
[58] Field of Search ...................... 514/316; 546/187

[56] References Cited

U.S. PATENT DOCUMENTS 5,378,712  1/1995  Alig et al. ................ 514/315

FOREIGN PATENT DOCUMENTS 0478363  4/1992  European Pat. Off. .
5148204  6/1993  Japan .

OTHER PUBLICATIONS

Alig et al., "Low Molecular Weight, Non–Peptide Fibrinogen Receptor Antagonists," *J. Med. Chem.*, vol. 35, No. 23, pp. 4393–4407 (1992).

Hartman et al., "Non–Peptide Fibrinogen Receptor Antagonists," *J. Med. Chem.*, vol. 35, No. 24, pp. 4640–4642 (1992).

Patent Abstracts of Japan, vol. 17, No. 180 (C–1046) [5809], pp. 54–56, (1993).

*Primary Examiner*—C. Warren Ivy
*Assistant Examiner*—Garth M. Dahlen
*Attorney, Agent, or Firm*—Birch, Stewart, Kolasch & Birch, LLP

[57] ABSTRACT

The present invention relates to an novel dipiperidine derivative represented by formula (1), or a pharmaceutically acceptable salt thereof;

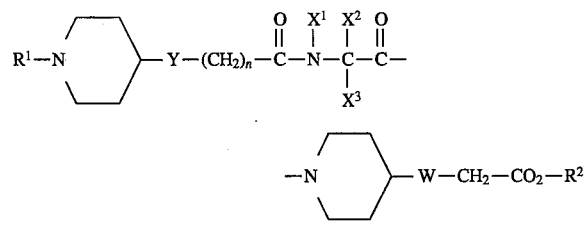

wherein $R^1$ represents a hydrogen atom or a lower alkyl group; Y represents a single bond or an oxygen atom; n represents 1, 2 or 3; W represents a methylene group or an oxygen atom; $R^2$ represents a hydrogen atom or a carboxyl modifying group which can be eliminated in vivo; $X^1$ and $X^3$ are the same or different and each represents a hydrogen atom or a lower alkyl group.

This compound is useful as platelet aggregation inhibitors, cancer metastasis inhibitors, wound remedies or bone resorption inhibitors.

11 Claims, No Drawings

DIPIPERIDINE DERIVATIVES

This application is a 371 of PCT/JP94/00908 filed Jun. 6, 1994.

TECHNICAL FIELD

The present invention relates to novel dipiperidine derivatives which are useful as platelet aggregation inhibitors, cancer metastasis inhibitors, wound remedies or bone resorption inhibitors.

BACKGROUND ART

Heretofore, proteins that participate in the adhesion of cells to interstitial connective tissues and have various physiological activities relevant to the cellular function of animal cells have been referred to as cell adhesion-activating proteins. As such proteins, for example, known are fibronectin, laminin, vitronectin, etc.

Further, it is known that the core sequence of the cell-bonding site of these proteins is comprised of arginine-glycine-aspartic acid, Arg-Gly-Asp (hereinafter referred to as RGD sequence: see Pierschbachr, M. D. et al, Nature, 309, 30 (1984); Suzuki, S. et al, J. Biol. Chem., 259, 15307 (1984); Plow, E. et al, Proc. Natl. Acad. Sci. USA, 82, 8057 (1985)).

It is known that fibrinogen existing in plasma interacts with platelet membrane glycoprotein IIb/IIIa complex via the RGD sequence thereby causing aggregation of platelets, and since a synthetic peptide having the RGD sequence inhibits the interaction between fibrinogen and the platelet membrane glycoprotein IIb/IIIa complex, it is considered that such a synthetic peptide will be effective as a platelet aggregation inhibitor (see Phillips, D. R., Cell, 65, 359 (1991)). Further, it is also known that a snake venom-derived peptide having the RGD sequence significantly inhibits the born resorption by osteoclasts (see Sato, Met al, J. Cell Biol., 111, 1713 (1990)).

It is considered that fibronectin participates in the adhesion of cells to interstitial connective tissues and also in differentiation and growth of cells in such a way that it adheres to the receptor of adhesive cells via its RGD sequence while transmitting its information to the cells (see Yamada, K. M., Ann. Rev. Biochem., 52, 761 (1983)).

Since fibronectin stimulates the wandering ability of fibroblasts and macrophages, it is considered that it can be applied to the remedy of wounds and to the control of the function of immunological competence. In particular, the local remedy of corneal disorders with fibronectin by utilizing its wound remedy-promoting effect has already been attempted (see Fujikawa, L. S. et al, Lab. Invest., 45, 120 (1981)). In addition, cell adhesion-activating proteins have been specifically noted as substances that participate in cancer metastasis. During the process of cancer metastasis, cancer cells are brought into contact with various host cells or biopolymers, and it is known that if cell adhesion-activating proteins such as fibronectin and laminin exist in the process, cancer cells form multicellular masses thereby more facilitating the growth and existence of the cancer cells themselves.

On the other hand, it has been confirmed that the adhesive core of fibronectin, tripeptide Arg-Gly-Asp (see Humphries, M. J. et al, Science, 233, 467 (1986) and the adhesive core of laminin, pentapeptide Tyr-Ile-Gly-Ser-Arg (see Iwamoto, Y. et al, Science, 238, 1132 (1987)) inhibit cancer metastasis.

As mentioned above, cell adhesion-activating proteins such as fibrinogen, fibronectin, laminin and others have various physiological activities, and pharmaceutically-active substances that selectively interact with the receptors of such proteins are expected to be applicable to preventives or remedies for various disorders. However, the peptides mentioned above have problems in that their specificity to the receptors and their absorbability and stability in vivo are low.

On the other hand, non-peptidic compounds that interact with the receptors of cell adhesion-activating proteins have been reported, for example, in J. Med. Chem.,35, 4393 (1992), EP 505868, Japanese Patent Laid-Open No. 4-288051, etc. However, none of these that have heretofore been reported is satisfactory for clinical use.

Under-the situation, it has been desired to develop platelet aggregation inhibitors, cancer metastasis inhibitors, wound remedies or bone resorption inhibitors which interact more selectively with cell adhesion-activating proteins such as fibrinogen, fibronectin and others and which have more excellent in vivo absorbability and stability.

DISCLOSURE OF THE INVENTION

The present inventors have assiduously studied and, as a result, have found novel dipiperidine derivatives that interact selectively with the receptors of cell adhesion-activating proteins such as fibrinogen, fibronectin and others.

Specifically, the gist of the present invention is in the following:

(1) A compound represented by formula (1) or a pharmaceutically acceptable salt thereof:

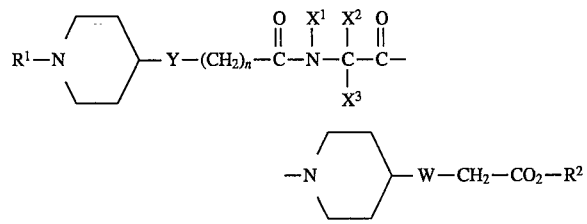

wherein $R^1$ represents a hydrogen atom or a lower alkyl group; Y represents a single bond or an oxygen atom; n represents 1, 2 or 3; W represents a methylene group or an oxygen atom; $R^2$ represents a hydrogen atom or a carboxyl modifying group which can be eliminated in vivo; $X^1$ and $X^3$ are the same or different and each represents a hydrogen atom or a lower-alkyl group; $X^2$ represents a hydrogen atom, a lower alkyl group, an aryl group, —$CHX^4OX^5$ (wherein $X^4$ represents a hydrogen atom or a methyl group; $X^5$ represents a hydrogen atom or a hydroxyl modifying group), —$CH_2CH_2OX^5$ (wherein $X^5$ represents the same meaning as above), —$CX^4{}_2SX^6$ (wherein $X^4$ represents the same meaning as above; $X^6$ represents a hydrogen atom or a thiol modifying group), —$CH_2CH_2S(O)_m CH_3$ (wherein m represents 0, 1 or 2), —$(CH_2)_p COOX^7$ (wherein p represents 1 or 2; $X^7$ represents a hydrogen atom or a carboxyl modifying group), —$(CH_2)_p CONHX^8$ (wherein p represents the same meaning as above; $X^8$ represents a hydrogen atom or an amide modifying group), —$(CH_2)_q NHX^9$ (wherein q represents 3 or 4; $X^9$ represents a hydrogen atom or an amino modifying group), —$(CH_2)_q NHC(=NH)NHX^{10}$ (wherein q represents the same meaning as above; $X^{10}$ represents a hydrogen atom or a guanidino modifying group), or —$(CH_2), X^{11}$ (wherein $X^{11}$ represents a halogen atom, a cycloalkyl group, an aryl group, a substituted aryl group, a heterocyclic group or a substituted heterocyclic group; r represents 1 or 2); provided that $X^1$ and $X^2$ may be combined together to form a trimethylene or tetramethylene group, or $X^2$ and $X^3$ may be combined together to form a pentamethylene group;

(2) A compound according to (1) or a pharmaceutically acceptable salt thereof, wherein $X^1$ is a hydrogen atom or a lower alkyl group, $X^2$ is a hydrogen atom, a lower alkyl group, —$CHX^4OX^5$ (wherein $X^4$ and $X^5$ represent the same meanings as above) or —$(CH^2)_r X^{11}$ (wherein $X^{11}$ and r represent the same meanings as above), or $X^1$ and $X^2$ are combined together to form a trimethylene or tetramethylene group;

(3) A compound according to (1) or (2), or a pharmaceutically acceptable salt thereof, wherein Y is an-oxygen atom and n is 1, or Y is a single bond and n is 2;

(4) A compound according to any one of (1) to (3), or a pharmaceutically acceptable salt thereof, wherein $R^1$ is a hydrogen atom;

(5) A platelet aggregation inhibitor containing as the active ingredient a compound according to any one of (1) to (4), or a pharmaceutically acceptable salt thereof;

(6) A cancer metastasis inhibitor containing as the active ingredient a compound according to any one of (1) to (4), or a pharmaceutically acceptable salt thereof;

(7) A wound remedy containing as the active ingredient a compound according to any one of (1) to (4), or a pharmaceutically acceptable salt thereof;

(8) A bone resorption inhibitor containing as the active ingredient a compound according to any one of (1) to (4), or a pharmaceutically acceptable salt thereof;

(9) A method for inhibiting platelet aggregation by administering a compound according to any one of (1) to (4), or a pharmaceutically acceptable salt thereof;

(10) A method for inhibiting cancer metastasis by administering a compound according to any one of (1) to (4), or a pharmaceutically acceptable salt thereof;

(11) A method for curing wounds by administering a compound according to any one of (1) to (4), or a pharmaceutically acceptable salt thereof;

(12) A method for inhibiting bone resorption by administering a compound according to any one of (1) to (4), or a pharmaceutically acceptable salt thereof;

(13) Use of a compound according to any one of (1) to (4), or a pharmaceutically acceptable salt thereof for remedy or prevention of disorders of human beings or animals.

As the lower alkyl group as referred to herein, there is, for example, a straight or branched alkyl group having from 1 to 6 carbon atoms, which specifically includes methyl, ethyl, propyl, 1-methylethyl, butyl, 1-methylpropyl, 2-methylpropyl, 1,1-dimethylethyl, pentyl, 1-methylbutyl, 2-methylbutyl, 1-ethylpropyl, hexyl, 1-methylpentyl, 2-methylpentyl, 1-ethylbutyl and others.

As the cycloalkyl group, there is, for example, a cycloalkyl group having from 5 to 7 carbon atoms, which specifically includes cyclopentyl, cyclohexyl, cycloheptyl and others.

As the aryl group, there is, for example, an aryl group having from 6 to 10 carbon atoms, which specifically includes phenyl, 1-naphthyl, 2-naphthyl and others.

As the substituted aryl group, there is, for example, an aryl group substituted by from 1 to 9 substituents selected optionally from the group consisting of a halogen atom, a hydroxyl group, a lower alkyl group, a lower alkyloxy group, a methylenedioxy group, a lower acyloxy group, an amino groups, an amidino group, a guanidino group, an aminomethyl group, a nitro group, a cyano group, a carboxyl group, a lower alkyloxycarbonyl group, a lower alkanoyl group and a benzyloxy group, which specifically includes 4-fluorophenyl, 3-chlorophenyl, 4-chlorophenyl, 3-bromophenyl, 4-bromophenyl, 4-iodophenyl, 2,4-dichlorophenyl, 4-hydroxyphenyl, 3,4-dihydroxyphenyl, 4-methylphenyl, 4-methoxyphenyl, 3,4-dimethoxyphenyl, 4-ethoxyphenyl, 3,4-methylenedioxyphenyl, 4-aminophenyl, 4-guanidinophenyl, 4-aminomethylphenyl, 4-cyanophenyl, 4-carboxyphenyl, 4-acetylphenyl, 4-chloro-1-naphthyl, 4-amidinophenyl, 4-nitrophenyl, 4-ethoxycarbonylphenyl, 4-acetoxyphenyl, 4-benzyloxyphenyl, 2-fluoro-4-hydroxyphenyl, 3-fluoro-4-hydroxyphenyl, 3,5-dibromo-4-hydroxyphenyl, 3,5-diiodo-4-hydroxyphenyl and others.

As the heterocyclic group, there is, for example, a mono- or bi-cyclic heterocyclic group having from 1 to 4 hetero atoms selected optionally from the group consisting of oxygen, nitrogen and sulfur atoms, which specifically includes 4-imidazolyl, 3-indolyl, 2-quinolyl, 4-pyridyl, 2-furyl, 2-thienyl and others.

As the substituted heterocyclic group, there is, for example, a heterocyclic group substituted by substituent(s) optionally selected from the group consisting of a lower alkyl group, a lower alkanoyl group, a lower alkyloxycarbonyl group, a lower alkylsulfonyl group, a 4-toluenesulfonyl group, a benzenesulfonyl group and a benzyl group, and this specifically includes 1-benzyl 4-imidazolyl, 1-(4-toluenesulfonyl)-4-imidazolyl, 1-benzyloxycarbonyl-4-imidazolyl, 1-formyl-3-indolyl, 1-methyl-3-indolyl and others.

The halogen atom includes, for example, fluorine, chlorine, bromine and iodine atoms.

As the lower alkanoyl group, for example, there is a straight or branched alkanoyl group having 5 or less carbon atoms, which specifically includes formyl, acetyl, propanoyl, butanoyl, 2-methylpropanoyl, pentanoyl, pivaloyl and others.

As the lower acyloxy group, there is, for example, a straight or branched acyloxy group having 5 or less carbon atoms, which specifically includes formyloxy, acetoxy, propanoyloxy, butanoyloxy, 2-methylpropanoyloxy, pentanoyloxy, pivaloyloxy and others.

As the carboxyl modifying group which can be eliminated in vivo, there are, for example, a lower alkyl group such as methyl, ethyl, propyl or the like; cyclohexyl; benzyl; a lower alkyl group substituted at the 1-position by —$OCOE^1$ (wherein $E^1$ represents a lower alkyl group, a cycloalkyl group, an aryl group, or a heterocyclic group), such as acetoxymethyl, 1-acetoxyethyl, 1-acetoxy-1-phenylmethyl, pivaloyloxymethyl, 1-pivaloyloxyethyl or the like; a lower alkyl group substituted at the 1-position by —$OCOOE^2$ (wherein $E^2$ represents a lower alkyl group, a cycloalkyl group, an aryl group, or a heterocyclic group), such as 1-methoxycarbonyloxyethyl, 1-ethoxycarbonyloxyethyl or the like; a lower alkyl group substituted by substituted heterocyclic group(s), such as 5-methyl-2-oxo-1,3-dioxolen-4-ylmethyl, 2-(1-morpholinyl)ethyl or the like; a heterocyclic group such as 5-oxo-2-tetrahydrofuranyl, 1,3-dihydro-3-oxo-1-isobenzofuranyl or the like; a substituted aryl group such as 5-indanyl or the like; and 3-dimethylamino-2-(dimethylaminomethyl)propyl, 2-dimethylaminoethyl, 2-diethylaminoethyl, methoxycarbonylmethyl, 2-dimethylaminocyclohexyl and others. Especially preferred are methyl, ethyl, acetoxymethyl, 1-acetoxyethyl, 1-acetoxy-1- phenylmethyl, pivaloyloxymethyl, 1-pivaloyloxyethyl, 1-methoxycarbonyloxyethyl, 1-ethoxycarbonyloxyethyl, 5-methyl-2-oxo-1,3-dioxolen-4-ylmethyl, 2-(1-morpholinyl)ethyl, 5-oxo-2-tetrahydrofuranyl, 1,3-dihydro-3-oxo-1-isobenzofuranyl, 5-indanyl, 3-dimethylamino-2-(dimethylaminomethyl)propyl, 2-dimethylaminoethyl, 2-diethylaminoethyl, methoxycarbonylmethyl, 2-dimethylaminocyclohexyl and the like.

As the hydroxyl, thiol, carboxyl, amide, amino or guanidino modifying group, for example, usable are protecting groups for side chains of amino acids such as those described in "The Peptide", Vols. 1, 2, 3 and 5 (Academic Press: 1979, 1980, 1981, 1983) or Izumiya et al, "Bases and Experiments for Peptide Synthesis" (Maruzen, 1985).

As the hydroxyl modifying group, there is an ether-type modifying group or an acyl-type modifying group. The ether-type modifying group includes, for example, methyl, benzyl, 2-nitrobenzyl, 2,6-dichlorobenzyl, t-butyl and others. The acyl-type modifying group, for example, includes a lower alkanoyl group and the like, such as acetyl or others.

As the thiol modifying group, there are a sulfide-type modifying group and the like, such as benzyl, 4-methylbenzyl, 4-nitrobenzyl, 4-methoxybenzyl, acetamidomethyl or others.

As the carboxyl modifying group, there are an ester-type modifying group and the like. The ester-type modifying group includes, for example, methyl, ethyl, 2,2,2-trichloroethyl, benzyl, 4-methoxybenzyl, diphenylethyl, t-butyl and others.

The amide modifying group includes 2,4-dimethoxybenzyl and others.

As the amino modifying group, there are an urethane-type modifying group, an acyl-type modifying group and the like. The urethane-type modifying group includes, for example, benzyloxycarbonyl, 4-nitrobenzyloxycarbonyl, 4-methoxybenzyloxycarbonyl, 2-methanesulfonylethoxycarbonyl, 2,2,2-trichloroethoxycarbonyl, t-butyloxycarbonyl and others. The acyl-type modifying group includes, for example, formyl, acetyl, benzoyl, trifluoroacetyl and others.

The guanidino modifying group includes benzyloxycarbonyl, t-butyloxycarbonyl, 4-toluenesulfonyl, 4-methoxybenzenesulfonyl, nitro and others.

In case that a compound represented by formula (1) has asymmetric carbon(s), it may be in the form of a mixture of optically active isomers, racemates or diastereomers.

Preferred examples of $X^1$ and $X^2$ in formula (1) are such that $X^1$ is a hydrogen atom or a lower alkyl group and $X^2$ is a hydrogen atom, a lower alkyl group, —$CHX^4OX^5$ (wherein $X^4$ and $X^5$ represent the same meanings as mentioned above) or -$(CH_2)_r X^{11}$ (wherein $X^{11}$ and r represent the same meanings as mentioned above). Also preferred are such that $X^1$ and $X^2$ are combined together to form a trimethylene or tetramethylene group. Especially preferably, $X^2$ is —$CH_2X^{12}$ (wherein $X^{12}$ represents a cycloalkyl group, an aryl group, a substituted aryl group, a heterocyclic group or a substituted heterocyclic group), and most preferably, it is a lower alkyloxybenzyl group or a hydroxybenzyl group. Preferred examples of $R^1$ and $X^3$ in formula (1) are hydrogen atoms.

Compounds represented by formula (1) can be produced for example according to a 2-step process such as that mentioned below.

Step 1: A compound of formula (2) is condensed with a compound of formula (3), and the amino protecting group is removed to obtain a compound of formula (4).

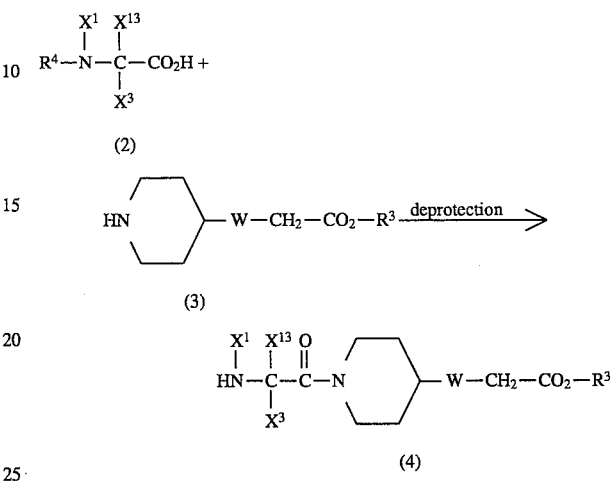

wherein W represents the same meaning as mentioned above; $R^3$ represents a lower alkyl group; $R^4$ represents an amino protecting group; $X^1$ and $X^3$ are the same or different and each represents a hydrogen atom or a lower alkyl group; $X^{13}$ represents a hydrogen atom, a lower alkyl group, an aryl group, —$CHX^4OX^{14}$ (wherein $X^4$ represents the same meaning as above; $X^{14}$ represents a hydroxyl modifying or protecting group), —$CH_2CH_2OX^{14}$ (wherein $X^{14}$ represents the same meaning as above), —$CX^4{}_2SX^{15}$ (wherein $X^4$ represents the same meaning as above; $X^{15}$ represents a thiol modifying or protecting group), —$CH_2CH_2S(O)_m CH_3$ (wherein m represents the same meaning as above), —$(CH_2)_p COOX^{16}$ (wherein p represents the same meaning as above; $X^{16}$ represents a carboxyl modifying or protecting group), —$(CH_2)_p CONHX^{17}$ (wherein p represents the same meaning as above; $X^{17}$ represents an amide modifying or protecting group), —$(CH_2)_q NHX^{18}$ (wherein q represents the same meaning as above; $X^{18}$ represents an amino modifying or protecting group), —$(CH_2)_q NHC(=NH)NHX^{19}$ (wherein q represents the same meaning as above; $X^{19}$ represents a guanidino modifying or protecting group) or —$(CH_2)_r X^{11}$ (wherein $X^{11}$ and r represent the same meanings as above); provided that $X^1$ and $X^{13}$ may be combined together to form a trimethylene or tetramethylene group, or $X^{13}$ and $X^3$ may be combined together to form a pentamethylene group.

Step 2: A compound of formula (4) is condensed with a compound of formula (5), optionally $R^3$ is converted into a hydrogen atom or a carboxyl modifying group which can be eliminated in vivo, and the protecting group(s) is/are removed to obtain a compound of formula (1).

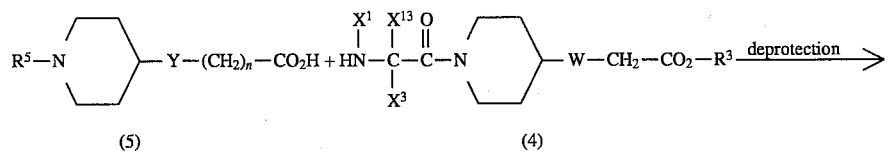

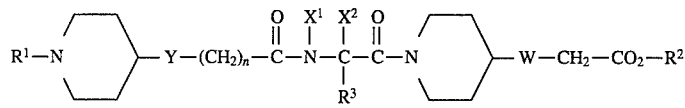

(1)

wherein $R^1$, $R^2$, $R^3$, Y, n, W, $X^1$, $X^2$, $X^3$ and $X^{13}$ represent the same meanings as above; $R^5$ represents a lower alkyl group or an amino protecting group.

Compounds of formula (2) are protected amino acids which are generally used in peptide chemistry, and many of these are available as commercial products in the market. These compounds can be produced by introducing an amino protecting group and optionally other modifying groups and protecting groups into an amino acid that can be produced according to the method described in R. M. Williams, "Synthesis of Optically Active α-Amino Acids" (Pergamon Press, 1989) or into a commercially available free amino acid, for example, according to the same method as that described in "The Peptide", Vols. 1, 2, 3 and 5 (Academic Press, 1979, 1980, 1981, 1983) or Izumiya et al, "Bases and Experiments of Peptide Synthesis" (Maruzen, 1985). Compounds of formula (2) wherein the amino group at the α-position is substituted by a lower alkyl group, can be produced by the same method as that described in Can. J. Chem., 55, 906 (1977).

Compounds of formula (3) can be produced, for example, by the same method as that described in J. Med. Chem., 35, 4393 (1992) or J. Am. Chem. Soc., 65, 2460 (1943), and optionally the carboxyl group therein may be esterified.

Compounds of formula (5) can be produced, for example, by the same method as that described in J. Med. Chem., 35, 4393 (1992) or J. Am. Chem. Soc., 65, 2460 (1943), and optionally the amino group therein is alkylated or protected. Alternatively, these can also be produced in the same manner as in the synthesis of Compound (10), Compound (13) and Compound (16) in the examples mentioned hereinunder. Alkylation of the amino group at the α-position can be executed, for example, by treating with $NaBH_3CN$ or the like in the presence of an aldehyde.

The condensation can be executed by known methods, for example, by the methods described in "The Peptide", Vols. 1, 2, 3 and 5 (Academic Press, 1979, 1980, 1981, 1983) or Izumiya et al, "Bases and Experiments of Peptide Synthesis" (Maruzen, 1985), namely, condensation methods such as an azide method, a mixed acid anhydride method, a dicyclohexylcarbodiimide method, a 1-(3-dimethylaminopropyl)-3-ethylcarbodiimide method, a benzotriazolyl-N-hydroxytrisdimethylaminophosphonium hexafluorophosphate method, an active ester method (an N-hydroxysuccinimide ester method, a p-nitrophenylester method, etc.), a Woodward reagent K method, a carbonyldiimidazole method or the like. For example, a free amine and a carboxylic acid are stirred in an inert solvent such as N,N-dimethylformamide, dichloromethane, acetonitrile or the like, under treating with a condensing agent such as 1-(3-dimethylaminopropyl)-3-ethylcarbodiimide hydrochloride or the like, at from 0° C. to 40° C. for from 1 to 24 hours. If desired, this reaction may be made in the presence of an additive such as 1-hydroxybenzotriazole or the like, or in the presence of a base such as triethylamine or the like.

As the protecting group for an amino, carboxyl, hydroxyl, thiol, amide or guanidino group, for example, usable are protecting groups for side chains of amino acids such as those described in "The Peptide", Vols. 1, 2, 3 and 5 (Academic Press, 1979, 1980, 1981, 1983) or Izumiya et al, "Bases and Experiments of peptide synthesis" (Maruzen, 1985); and the protecting group can be introduced or removed according to the methods described in these references.

The amino protecting group may be any one that is generally used in peptide chemistry, including, for example, an urethane-type protecting group such as t-butyloxycarbonyl, benzyloxycarbonyl or the like, and an amide-type protecting group such as formyl, acetyl or the like. As the amino protecting group, preferred is one that can be removed without removing other modifying groups. Regarding the removal of the amino protecting group, for example, t-butyloxycarbonyl group or the like can be removed by using an acid such as trifluoroacetic acid, hydrogen chloride/dioxane or the like; benzyloxycarbonyl can be removed by hydrogenation in the presence of a noble metal catalyst such as palladium on carbon (Pd/C) or the like; formyl or the like can be removed by using hydrazine acetate or the like; and trifluoroacetyl or the like can be removed by using an aqueous solution of sodium hydroxide or the like.

As the carboxyl protecting group, there is an ester-type modifying group or the like. The ester-type modifying group includes, for example, methyl, ethyl, t-butyl, 2,2,2-trichloroethyl, benzyl, 4-methoxybenzyl, diphenylethyl and others. Regarding the removal of the protecting group of this type, for example, methyl, ethyl or the like can be removed by using a base such as an aqueous solution of sodium hydroxide or the like; t-butyl or the like can be removed by using an acid such as trifluoroacetic acid, hydrogen chloride/dioxane or the like; 2,2,2-trichloroethyl or the like can be removed by using Zn/acetic acid or the like; benzyl or the like can be removed by hydrogenation in the presence of a noble metal catalyst such as Pd/C or the like.

The hydroxyl protecting group such as benzyl or the like can be removed, for example, by hydrogenation in the presence of a noble metal such as Pd/C or the like.

The thiol protecting group such as acetamidomethyl or the like can be removed, for example, by using an acetic acid solution of iodine or the like.

The amide protecting group such as 2,4-dimethoxybenzyl or the like can be removed by using trifluoroacetic acid or the like.

As the guanidino protecting group, there is 4-toluenesulfonyl, nitro or the like. 4-Toluenesulfonyl or the like can be removed by using hydrogen fluoride, and nitro or the like can be removed by hydrogenation in the presence of a noble metal such as Pd/C or the like.

Compounds of formula (1) can be purified by ordinary purifying methods, for example, by recrystallization or high-performance liquid chromatography.

As a pharmaceutically acceptable salt, there are a pharmaceutically acceptable salt with an acid and salt with a base. The salt with an acid includes a salt with an inorganic acid such as hydrochloride, sulfate, phosphate, etc.; and a salt with an organic acid such as acetate, butyrate, methanesulfonate, trifluoroacetate, citrate, fumarate, maleate, succinate, salicylate, etc. The salt with a base includes a salt with an inorganic base and a salt with an organic base. The salt with an inorganic base includes an alkali metal salt such as sodium salt, potassium salt, etc.; an alkaline earth metal salt such as calcium salt, magnesium salt, etc.; and ammonium salt, etc. The salt with an organic base includes a salt with a basic amino acid such as arginine salt, lysine salt etc.

These salts can be easily produced by known means. To produce an acetate, for example, a compound of formula (1) is dissolved in water and a necessary amount of acetic acid is added thereto.

Animals to which a compound of the present invention can be administered are not specifically limited, including not only human beings but also various mammals such as mouse, rat, dog, cat, cattle, horse, goat, sheep, rabbit, pig, etc.

To administer the compounds to these animals and human beings, any ordinary administration routes can be used, which include, for example, peroral, intramuscular, intravenous, subcutaneous, intraabdominal and nasal administration routes. A dose of the compound and the frequency of administration vary, depending on the type of the animal to which the compound is administered, the administration route, the condition of the animal, the weight of the animal and others, and are therefore not specifically limited. To human beings, for example, the compound is administered in an amount of from about 1 mg/adult/day to about 1 g/adult/day, once or several times a day. The form of the dosage includes, for example, powders, fine granules, granules, tablets, capsules, suppositories, injections, nasal spray, etc. These dosage forms can be formulated by ordinary methods using ordinary formulation carriers. For example, when peroral dosage forms are formulated, a binder, a disintegrator, a lubricant, a colorant or other additive are optionally added to the compound and then formed into tablets, granules, powders, capsules and others by ordinary methods. When injections are formulated, a pH-adjusting agent, a buffer, a stabilizer, a solubilizer and other additives are optionally added to the compound and formed into injections by ordinary methods.

According to the present invention, the supply of novel dipiperidine derivatives which are useful as platelet aggregation inhibitors, cancer metastasis inhibitors, wound remedies or bone resorption inhibitors has been realized.

BEST MODE FOR CARRYING OUT THE INVENTION

The present invention is described in more detail hereinunder, with reference to typical examples of the compounds of the present invention and working examples of the present invention, but the present invention is not restricted by these typical examples and working examples. The following abbreviations are used in the text.

| Abbreviations | Name |
|---|---|
| DMF | N,N-dimethylformamide |
| HOBT.H$_2$O | 1-hydroxybenzotriazole hydrate |
| WSC.HCl | 1-(3-dimethylaminopropyl)-3-ethylcarbodiimide hydrochloride |
| TFA | trifluoroacetic acid |
| THF | tetrahydrofuran |
| Z | benzyloxycarbonyl |
| Tyr | tyrosine residue |
| Tyr(Me) | O-methyltyrosine residue |
| Phe | phenylalanine residue |
| Val | valine residue |
| Ala | alanine residue |
| Gly | glycine residue |
| Pro | proline residue |
| Leu | leucine residue |
| Ile | isoleucine residue |
| Trp | tryptophan residue |
| Ser | serine residue |
| tBu | t-butyl |
| Boc | t-butyloxycarbonyl |
| (Boc)$_2$O | di-t-butyl dicarbonate |

Typical examples of the compounds of the present invention are shown in Table 1 and Table 2 below.

TABLE 1

$$H-N\diagup\hspace{-0.3em}\diagdown-O-CH_2-\underset{\underset{}{\overset{O}{\|}}}{C}-\underset{\underset{X^3}{|}}{\overset{\overset{X^1}{|}}{N}}-\underset{}{\overset{\overset{X^2}{|}}{C}}-\underset{\underset{}{\overset{O}{\|}}}{C}-N\diagup\hspace{-0.3em}\diagdown-O-CH_2-CO_2-H$$

| number | X$^1$ | X$^2$ | X$^3$ |
|---|---|---|---|
| 1 | H | —CH$_2$—C$_6$H$_4$—OEt | H |
| 2 | H | —CH$_2$—C$_6$H$_5$ | H |
| 3 | H | —CH$_3$ | H |
| 4 | H | —CH$_2$OCOCH$_3$ | H |

TABLE 1-continued

H—N⟨piperidine⟩—O—CH$_2$—C(=O)—N(X$^1$)—C(X$^2$)(X$^3$)—C(=O)—N⟨piperidine⟩—O—CH$_2$—CO$_2$—H

| number | X$^1$ | X$^2$ | X$^3$ |
|---|---|---|---|
| 5 | H | —CH$_2$—(3-indolyl) | H |
| 6 | H | phenyl | H |
| 7 | H | —CH$_2$—(3-iodo-4-hydroxyphenyl) | H |
| 8 | H | —CH$_2$—(4-bromophenyl) | H |
| 9 | H | —(CH$_2$)$_4$NH$_2$ | H |
| 10 | | —(CH$_2$)$_3$— | |
| 11 | H | —(CH$_2$)$_4$— | |

TABLE 2

R$^1$—N⟨piperidine⟩—Y—(CH$_2$)$_n$—C(=O)—N(X$^1$)—C(CH$_2$-C$_6$H$_4$-OCH$_3$)(X$^3$)—C(=O)—N⟨piperidine⟩—W—CH$_2$—CO$_2$—R$^2$

| number | R$^1$ | Y | n | X$^1$ | X$^3$ | W | R$^2$ |
|---|---|---|---|---|---|---|---|
| 12 | H | single bond | 1 | H | H | —O— | H |
| 13 | CH$_3$ | single bond | 2 | H | H | —O— | H |
| 14 | H | single bond | 2 | H | H | —O— | CH$_2$CH$_3$ |
| 15 | H | single bond | 2 | CH$_3$ | H | —O— | H |
| 16 | CH$_3$ | —O— | 1 | H | H | —O— | H |
| 17 | H | —O— | 1 | CH$_3$ | H | —O— | H |
| 18 | H | —O— | 1 | H | CH$_3$ | —O— | H |
| 19 | H | —O— | 1 | H | H | —CH$_2$— | H |
| 20 | H | —O— | 1 | H | H | —O— | CH$_2$CH$_3$ |

EXAMPLE 1

Synthesis of
(1-N-(3-(4-piperidyl)propanoyl)-O-methyl-L-tyrosyl)-
4-piperridyloxy)acetic acid TFA salt (Compound
(12))

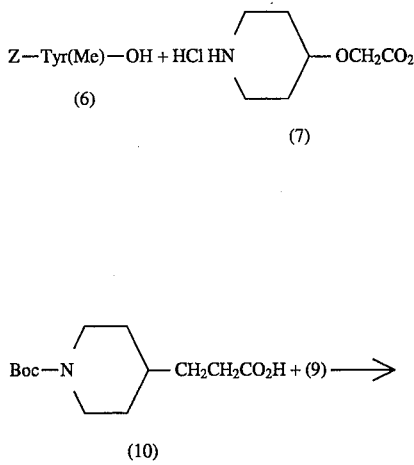

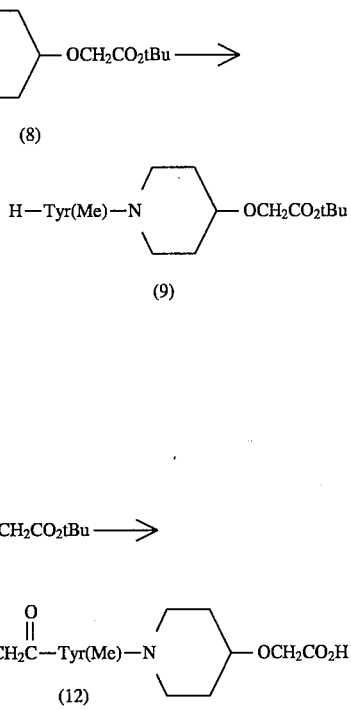

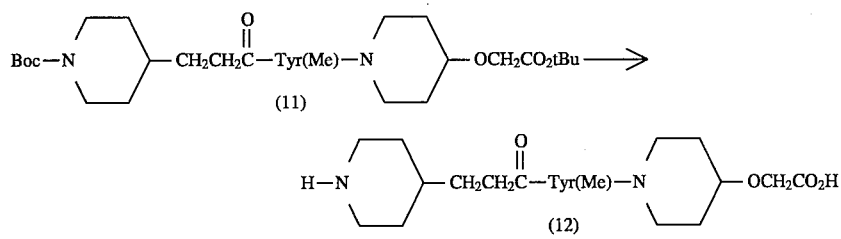

① Synthesis of t-butyl (4-Piperidyloxy)acetate hydrochloride (Compound (7))

6.0 g of t-butyl (4-piperidyloxy)acetate that had been obtained according to the method described in J. Med. Chem., 35, 4393 (1991) was treated with a small excess amount of HCl/ether while cooling with ice, and the resulting precipitate was filtered and dried to give 6.3 g of the hydrochloride of the ester as a white powder.

② Synthesis of Compound (8)

To a DMF (5 ml) solution of 150 mg of compound (7), were added 0.092 ml of triethylamine, 216 mg of compound (6) and 110 mg of HOBT·H$_2$O. Then, 138 mg of WSC·HCl was added while cooling with ice (at 5° C.) and stirred for 30 minutes at 5° C. and then overnight at room temperature. The reaction mixture was diluted with ethyl acetate and then washed with 1N HCl, saturated NaHCO$_3$ and brine (twice each). This was dried with magnesium sulfate, and the solvent was removed by distillation under a reduced pressure. Thus, 315 mg of compound (8) was obtained.

$^1$H-NMR (CDCl$_3$,δ): 1.47 (9H,s), 1.56–1.76 (4H,m), 2.86–2.94 (2H,m), 3.19–3.57 (4H,m), 3.70–3.81 (1H,m), 3.77 (3H,s), 3.94 (2H,s), 4.82–4.90 (1H,m), 5.02–5.14 (2H, m), 5.69–5.74 (1H,m), 6.62–6.85 (2H,m), 7.05–7.09 (2H, m), 7.33 (5H,br s) Mass (SIMS) 527 (M$^+$+1)

③ Synthesis of Compound (9)

To an ethanol (7 ml) solution of 315 mg of compound (8), was added 200 mg of 10% Pd/C (50% wet) and stirred in a hydrogen atmosphere for 2.5 hours at room temperature. The catalyst was removed by filtration, then the solvent was removed by distillation under a reduced pressure, and 267 mg of compound (9) was obtained as an oil.

④ Synthesis of 3-(1-t-buyloxycarbonyl-4-piperidyl)propane (Compound (10))

20 g of isonipecotic acid was dissolved in a mixed solution comprising 170 ml of 1N NaOH and 150 ml of dioxane, and 37.1 g of (Boc)$_2$O was added. After stirring overnight at room temperature, this was made acidic with 1N HCl and then extracted with ethyl acetate. The extract was washed with water and brine and dried with magnesium sulfate. The solvent was removed by distillation under a reduced pressure, and 33.9 g of a Boc-modified product was obtained.

To 400 ml of a methylene chloride solution of 20.0 g of the Boc-modified product, were added 9.7 g of triethylamine, 11.0 g of N-hydroxysuccinimide and 18.4 g of WSC·HCl, and these were stirred for 3 hours at room temperature. The reaction mixture was diluted with methylene chloride, washed twice with water and dried with sodium sulfate. The solvent was removed by distillation under a reduced pressure, and 29.0 g of a white solid was obtained. To a THF (400 ml) solution of 25.6 g of the white solid, was added 7.42 g of NaBH$_4$, and these were stirred for 2.5 hours at room temperature and then for 15 minutes at 50° C. The reaction mixture was cooled, 200 ml of 10% NH$_4$Cl was added to this, which was then extracted with ethyl acetate. The extract was washed with water and brine and dried with magnesium sulfate. The solvent was removed by distillation under a reduced pressure, and the residue was purified by silica gel chromatography (using hexane: ethyl acetate=1:1) to give 13.0 g of (1-t-butyloxycarbonyl-4-piperidyl)methanol as a white solid.

2.05 ml of oxalyl chloride was added to 30 ml of a methylene chloride solution of 2.2 ml of dimethylsulfoxide at −78° C. and stirred for 5 minutes. 10 ml of a methylene chloride solution of 2.0 g of the above-mentioned alcohol was added dropwise, and these were stirred for further 15 minutes. 5.2 ml of triethylamine was added, then heated up to room temperature and stirred for still further 30 minutes. Water was added to the reaction mixture, which was then extracted three times with ethyl acetate. The extract was washed with 1N HCl, saturated NaHCO$_3$ and brine (twice each). This was dried with magnesium sulfate, and the solvent was removed by distillation under a reduced pressure. Thus, 1.98 g of (1-t-butyloxycarbonyl-4-piperidine) carboxyaldehyde was obtained. 410 mg of 60% NaH was gradually added to 10 ml of a THF solution of 2.50 g of ethyl diethylphosphonoacetate in a nitrogen atmosphere below 40° C. and then stirred for 10 minutes. 10 ml of a THF solution of 1.98 g of the above-mentioned aldehyde was dropwise added below 35° C. and stirred for 2 hours at room temperature. Water was added to the reaction mixture, which was then extracted three times with ethyl acetate. The extract was washed with 1N HCl, saturated NaHCO$_3$ and brine (twice each). This was dried with magnesium sulfate, and the solvent was removed by distillation under a reduced pressure. The residue was purified by silica gel column chromatography (using hexane:ethyl acetate=4:1) to give 2.43 g of ethyl 3-(1-t-butyloxycarbonyl-4-piperidyl)-2-propenoate as an oil.

1.54 g of 10% Pd/C (50% wet) was added to 15 ml of an ethanol solution of 2.43 g of the thus-obtained ester and stirred in a hydrogen atmosphere at room temperature for 3 hours. The catalyst was removed by filtration, and the solvent was removed by distillation under a reduced pressure. Thus, 2.41 g of a residue was obtained. 13 ml of 1N NaOH was added to 20 ml of a methanol solution of 2.08 g of the residue and stirred at room temperature for 3 hours. The methanol was removed by distillation under a reduced pressure, and then the residue was made acidic with 1N HCl and extracted three times with ethyl acetate. This was washed with brine and dried with magnesium sulfate. The solvent was removed by distillation under a reduced pressure. Thus, 1.90 g of 3-(1-t-butyloxycarbonyl-4-piperidyl) propanoic acid was obtained as a white solid.

$^1$H-NMR (CDCl$_3$,δ): 1.00–1.20 (2H,m), 1.45 (9H,s), 1.55–1.72 (5H,m), 2.39 (2H,t,J=7Hz), 2.67 (2H,t,J=13Hz), 4.00–4.20 (2H,m)

⑤ Synthesis of Compound (11)

0.057 ml of triethylamine, 105 mg of compound (10) and 68 mg of HOBT·H$_2$O were added to a DMF (5 ml) solution of 144 mg of compound (9), then 85 mg of WSC·HCl was added while cooling with ice (at 5° C.), and these were stirred at 5° C. for 30 minutes and then overnight at room temperature. 10 ml of water was added to the reaction mixture, which was extracted three times with ethyl acetate. The organic layer was washed with 1N HCl, saturated NaHCO$_3$ and brine (twice each). This was dried with magnesium sulfate, and the solvent was removed by distillation under a reduced pressure. Thus, 236 mg of compound (11) was obtained as a white solid.

$^1$H-NMR (CDCl$_3$,δ): 1.05–1.32 (2H,m), 1.45 (9H,s), 1.47 (9H,s), 1.49–1.85 (9H,m), 2.17–2.23 (2H,m), 2.60–3.01 (6H,m), 3.14–3.59 (4H,m), 3.78 (3H,s), 3.94 (2H,s), 4.08–4.16 (1H,m), 5.09–5.17 (1H,m), 6.39–6.44 (1H,m), 6.78–6.85 (2H,m), 7.04–7.09 (2H,m) Mass (SIMS) 632 (M$^+$+1)

⑥ Synthesis of Compound (12)

92 mg of compound (11) was left at room temperature in TFA for 1 hour, then the TFA was removed by distillation under a reduced pressure, and the residue was purified by HPLC to obtain 87 mg of compound (12) as an oil. $^1$H-NMR (CD$_3$OD,δ): 1.05–2.00 (11H,m), 2.15–2.29 (2H,m), 2.79–3.40 (10H,m), 3.50–3.90 (3H,m), 3.76 (3H,s), 4.08 (1H,s), 4.09 (1H,s), 5.05 (1H,m), 6.80–6.90 (2H,m), 7.08–7.18 (2H,m) Mass (SIMS) 476 (M$^+$+1) HPLC Retention Time: 20.6 minutes (Column: YMC-ODS 4.6 mmΦ×25 cm, Detection: 220 nm, Eluents: A solution (0.1% TFA/water), B solution (0.1% TFA/acetonitrile), Flow Rate: 1 ml/min, Gradient: The concentration of B solution was increased by 10% at a rate of 1%/min. The same condition of HPLC was applied to the compounds in Example 2 to 18.)

EXAMPLE 2

Synthesis of (1-N-((4-piperidyloxy)acetyl)-O-methyl-L-tyrosyl)-4-piperidyloxy)acetic acid TFA salt (Compound (15))

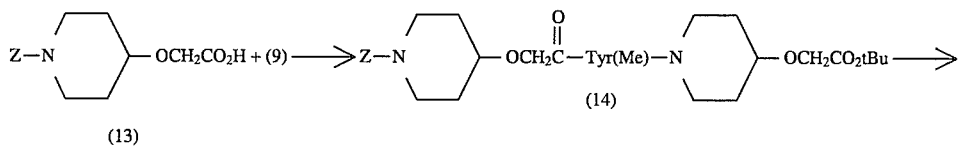

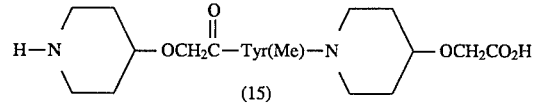

① Synthesis of (1-benzloxycarbonyl-4-piperidyloxy)acetic acid (compound (13))

11.0 9 of t-butyl (1-benzyloxycarbonyl-4-piperidyloxy) acetate that had been obtained according to the method described in J. Med. Chem., 35, 4393 (1992) was stirred in 3N HCl/dioxane at room temperature for 4 hours, and the solvent was removed by distillation under a reduced pressure. Thus, 9.2 g of (1-benzyloxycarbonyl-4-piperidyloxy) acetic acid was obtained as a pale yellow syrup.

$^1$H-NMR (CDCl$_3$,δ): 1.52–1.70 (2H,m), 1.78–1.9 (2H,m), 3.15–3.28 (2H,m), 3.56–3.68 (1H,m), 3.74–3.92 (2H,m), 4.17 (2H,s), 5.15 (2H,s), 7.28–7.42 (5H,m)

② Synthesis of Compound (14)

To a DMF (5 ml) solution of 123 mg of compound (9) were added 0.048 ml of triethylamine, 119 mg of compound (13) and 57 mg of HOBT·H$_2$O, and 71 mg of WSC·HCl was added while cooling with ice (at 5° C.). Then, these were stirred at 5° C. for 30 minutes and then at room temperature overnight. 10 ml of water was added to the reaction mixture, which was extracted three times with ethyl acetate. The organic layer was washed with 1N HCl, saturated NaHCO$_3$ and brine (twice each). This was dried with magnesium sulfate, and the solvent was removed by distillation under a reduced pressure. Thus, 214 mg of compound (14) was obtained as a white solid.

$^1$H-NMR (CDCl$_3$,δ): 1.10–1.83 (8H,m), 1.47 (9H,s), 2.88–4.18 (14H,m), 3.76 (3H,s), 3.94 (2H,s), 5.08–5.19 (1H,s), 5.13 (2H,s), 6.78–6.82 (2H,m), 7.05–7.10 (2H,m), 7.63 (5H,br s) Mass (SIMS) 668 (M$^+$+1)

③ Synthesis of Compound (15)

100 mg of 10% Pd/C was added to an ethanol (10 ml) solution of 105 mg of compound (14) and stirred in a hydrogen atmosphere for 2 hours at room temperature. The catalyst was removed by filtration, and the solvent was removed by distillation under a reduced pressure. 5 ml of TFA was added to the residue and left at room temperature for 1 hour, and the TFA was removed by distillation under a reduced pressure. The residue was purified by HPLC to give 57 mg of compound (15) as a white powder.

$^1$H-NMR (CD$_3$OD,δ): 1.18–2.09 (8H,m), 2.85–3.90 (14H, m), 3.77 (3H,s), 4.01 (2H,s), 4.10 (2H,s), 5.14 (1H,t,J=7Hz), 6.85 (2H,d,J=8Hz), 7.11 (2H,d,J=8Hz) Mass (SIMS) 478 (M$^+$+1) HPLC Retention Time: 20.2 minutes

EXAMPLE 3

Synthesis of
(1-(N-(4-(4-piperidyl)butanoyl)-O-methyl-L-tyrosyl)-4-piperidyloxy)acetic acid TFA salt
(Compound (18))

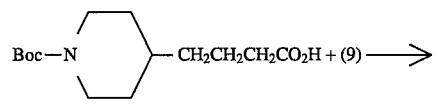

(16)

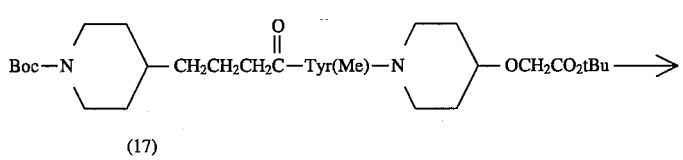

(17)

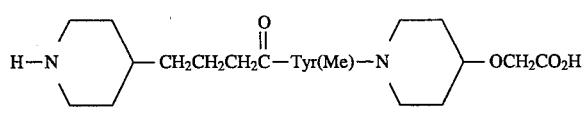

(18)

① Synthesis of 4-(1-t-butyloxycarbonyl-4-piperidyl)butanoic acid (Compound (16))

10.0 g of 4-piperidinone hydrochloride was dissolved in 100 mg of dioxane and an aqueous solution (50 ml) of 5.7 g of NaOH, 16.1 g of (Boc)$_2$O was added, and these were stirred for 2 hours while cooling with ice. The reaction mixture was diluted with ethyl acetate, and the organic layer was washed with an aqueous 10% citric acid solution, saturated NaHCO$_3$, brine (twice each) and dried with magnesium sulfate. The solvent was removed by distillation under a reduced pressure, and hexane was added to the residue. The precipitate was filtered and dried to give 7.55 g of 1-t-butyloxycarbonyl-4-piperidinone.

7.4 ml of 1.6M n-butyl lithium/hexane solution was dropwise added to a THF solution (30 ml) of 8.41 g of ethyl 4-diethylphosphonocrotonate below −50° C. and stirred for 15 minutes at −78° C. . To this was dropwise added 25 ml of a THF solution of 5.0 g of the above-mentioned 1-t-butyloxycarbonyl-4-piperidinone. This was stirred for 20 minutes at −78° C. and then for 2 hours at −10° C. The reaction mixture was diluted with water and extracted three times with ethyl acetate. The organic layer was washed with 1N HCl, saturated NaHCO$_3$, brine (twice each) and dried with magnesium sulfate. The solvent was removed by distillation under a reduced pressure. Thus, 7.70 g of ethyl 4-(1-t-butyloxycarbonyl-4-piperidylidene)-2-butenoate was obtained as a white solid.

960 mg of 10% Pd/C (50% wet) was added to a mixed solution comprising 20 ml of ethyl acetate and 40 ml of ethanol and containing 7.70 g of the ester obtained above, and stirred in a hydrogen atmosphere at room temperature for 6 hours. The catalyst was removed by filtration, and the solvent was removed by distillation under a reduced pressure. Thus, 7.76 g of ethyl 4-(1-t-butyloxycarbonyl-4piperidyl)butanoate was obtained as a white solid. The $^1$H-NMR spectrum of this product was the same as that in literature (Japanese Patent Laid-Open No. 4-288051).

An aqueous solution (2 ml) of 700 mg of NaOH was added to 15 ml of a methanol solution of 1.0 g of ethyl 4-(1-t-butyloxycarbonyl-4-piperidyl)butanoate and stirred for 1 hour at room temperature. The methanol was removed by distillation under a reduced pressure, and the residue was made acidic with 1N HCl and then extracted with ethyl acetate. This was washed with brine, dried with magnesium sulfate, and the solvent was removed by distillation under a reduced pressure. Thus, 0.91 g of 4-(1-t-butyloxycarbonyl-4-piperidyl)butanoic acid was obtained as a white solid.

$^1$H-NMR (CDCl$_3$,δ): 1.00–1.50 (6H,m), 1.45 (9H,s), 1.60–1.72 (3H,m), 2.35 (2H,t,J=7Hz), 2.67 (2H,t,J=8Hz), 4.00–4.15 (2H,m)

② Synthesis of Compound (17)

To 5 ml of a DMF solution of 56 mg of compound (9) were added 0.020 ml of triethylamine, 44 mg of compound (16) and 27 mg of HOBT·H$_2$O, and 34 mg of WSC·HCl was added while cooling with ice (at 5° C.) and stirred at 5° C. for 30 minutes and then at room temperature overnight. 10 ml of water was added to the reaction mixture, which was then extracted three times with ethyl acetate. The organic layer was washed with 1N HCl, saturated NaHCO$_3$, and brine (twice each). This was dried with magnesium sulfate, and the solvent was removed by distillation under a reduced pressure. Thus, 91 mg of compound (17) was obtained as a white solid.

③ Synthesis of Compound (18)

91 mg of compound (17) was left in TFA for 1 hour at room temperature, then the TFA was removed by distillation under a reduced pressure, and the residue was purified by HPLC to give 92 mg of compound (18) as an oil.

$^1$H-NMR (CD$_3$OD,$\delta$): 1.05–2.00 (13H,m), 2.20 (2H,t,J=7Hz), 2.80–3.40 (10H,m), 3.50–3.90 (4H,m), 3.76 (3H,s), 4.07 (1H,s), 4.09 (1H,s), 5.00–5.15 (1H,m), 6.80–6.90 (2H,m), 7.08–7.18 (2H,m) Mass (SIMS) 490 (M$^+$+1) HPLC Retention Time: 21.7 minutes

EXAMPLE 4

Synthesis of
(1-(N-(4-piperidyloxyacetyl)-L-tyrosyl)-
4-piperidyloxy)acetic acid TFA salt
(Compound (19))

In the same manner as in Example 2, 150 mg of compound (19) was produced as a white solid.

$^1$H-NMR (DMSO-d$_6$,$\delta$): 1.14–1.42 (2H,m), 1.56–1.96 (6H,m), 2.67–3.29 (7H,m), 3.46–4.15 (6H,m), 3.89 (2H,s), 4.03 (2H,s), 4.86–4.99 (1H,m), 6.64 (2H,d,J=7Hz), 6.97 (2H,d, J=7Hz), 7.73–7.86 (1H,m), 8.40 (1H,s) Mass (SIMS) 464 (M$^+$+1) HPLC Retention Time: 17.6 minutes

EXAMPLE 5

Synthesis of
(1-(N-(3-(4-piperidyl)propanoyl)-L-tyrosyl)-
4piperidyloxy)acetic acid TFA salt
(Compound (20))

In the same manner as in Example 1, 200 mg of compound (20) was produced as a white solid.

$^1$H-NMR (DMSO-d$_6$,$\delta$): 1.08–1.45 (7H,m). 1.52–1.80 (4H, m), 1.96–2.13 (2H,m), 2.54–3.30 (7H,m), 3.43–3.95 (5H, m), 4.02 (2H,s), 4.78–4.92 (1H,m), 6.64 (2H,d,J=7Hz), 6.99 (2H,d,J=7Hz), 8.10–8.30 (2H,m), 8.49 (1H,s) Mass (SIMS) 462 (M$^+$+1) HPLC Retention Time: 17.9 minutes

EXAMPLE 6

Synthesis of
(1-(N-(3-(4-piperidyl)propanoyl)-L-phenylalanyl)-
4-piperidyloxy)acetic acid TFA salt
(Compound (21))

In the same manner as in Example 1, 237 mg of compound (21) was produced as an oil.

$^1$H-NMR (DMSO-d$_6$,$\delta$): 1.00–1.43 (7H,m), 1.50–1.80 (4H, m), 1.95–2.13 (2H,m), 2.63–3.30 (8H,m), 3.45–3.92 (3H, m), 4.01 (2H,s), 4.88–5.00 (1H,m), 7.14–7.40 (5H,m), 8.20 (1H,s), 8.27 (1H,t,J=9Hz), 8.52 (1H,s) Mass (SIMS) 446 (M$^+$+1) HPLC Retention Time: 23.8 minutes

EXAMPLE 7

Synthesis of
(1-(N-(3-(4-piperidyl)propanoyl)-L-valyl)-
4-piperidyloxy)acetic acid TFA salt
(Compound (22))

In the same manner as in Example 1, 244 mg of compound (22) was produced as an oil.

$^1$H-NMR (DMSO-d$_6$,$\delta$): 0.75–0.90 (6H,m), 1.10–1.55 (7H, m), 1.70–2.25 (7H,m), 2.67–3.35 (6H,m), 3.50–4.00 (3H, m), 4.05 (2H,m), 4.47–4.60 (1H,m), 8.04 (1H,t,J=4Hz), 8.25 (1H,s), 8.56 (1H,s) Mass (SIMS) 398 (M$^+$+1) HPLC Retention Time: 18.2 minutes

EXAMPLE 8

Synthesis of
(1-(N-(3-(4-piperidyl)propanoyl)-L-alanyl)-
4-piperidyloxy)acetic acid TFA salt
(Compound (23))

In the same manner as in Example 1, 146 mg of compound (23) was produced as an oil.

$^1$H-NMR (DMSO-d$_6$,$\delta$): 1.05–1.56 (10H,m), 1.70–1.95 (4H, m), 2.05–2.20 (2H,m), 2.70–3.04 (3H,m), 3.19–4.10 (8H, m), 4.65–4.80 (1H,m), 8.12 (1H,t,J=8Hz), 8.26 (1H,s), 8.58 (1H,s) Mass (SIMS) 370 (M$^+$+1) HPLC Retention Time: 8.6 minutes

EXAMPLE 9

Synthesis of
(1-(N-(3-(4-piperidyl)propanoyl-glycyl)-
4-piperidyloxy)acetic acid TFA salt
(Compound (24))

In the same manner as in Example 1, 157 mg of compound (24) was produced as an oil.

$^1$H-NMR (DMSO-d$_6$,$\delta$): 1.15–1.60 (8H,m), 1.73–1.91 (3H, m), 2.17 (2H,t,J=7Hz), 2.73–2.90 (2H,m), 3.00–3.31 (3H, m), 3.53–3.89 (6H,m), 3.92 (2H,d,J=9Hz), 7.93 (1H,t,J=5Hz), 8.21 (1H,s), 8.51 (1H,s) Mass (SIMS) 356 (M$^+$+1) HPLC Retention Time: 6.9 minutes

EXAMPLE 10

Synthesis of
(1-(N-(3-(4-piperidyl)propanoyl)-L-prolyl)-
4-piperidyloxy)acetic acid TFA salt
(Compound (25))

In the same manner as in Example 1, 205 mg of compound (25) was produced as an oil.

$^1$H-NMR (DMSO-d$_6$,$\delta$): 0.95–1.96 (16H,m), 2.01–2.35 (2H, m), 2.71–3.10 (2H,m), 3.14–3.90 (8H,m), 3.92–4.13 (2H, m), 4.73–5.00 (1H,m), 8.28 (1H,s), 8.57 (1H,s) Mass (SIMS) 396 (M$^+$+1) HPLC Retention Time: 14.3 minutes

EXAMPLE 11

Synthesis of (1-(N-(3-(4-piperidyl)
propanoyl)-L-leucyl)-4-piperidyloxy)acetic acid
TFA salt (Compound (26))

In the same manner as in Example 1, 172 mg of compound (26) was produced as a white powder.

¹H-NMR (DMSO-d₆,δ): 0.86 (6H, d, J=5Hz), 1.13–1.63 (10H,m), 1.70–1.94 (4H,m), 2.03–2.21 (2H,m), 2.70–3.04 (2H,m), 3.10–3.35 (3H,m), 3.53–4.00 (6H,m), 4.70–4.84 (1H,m), 8.10 (1H,t,J=9Hz), 8.26 (1H,s), 8.56 (1H,s) Mass (SIMS) 412 (M⁺+1) HPLC Retention Time: 21.7 minutes

EXAMPLE 12

Synthesis of (1-(N-(3-(4-piperidyl)propanoyl)-L-isoleucyl)-4-piperidyloxy)acetic acid TFA salt (Compound (27))

In the same manner as in Example 1, 148 mg of compound (27) was produced as a white powder.
¹H-NMR (DMSO-d₆,δ): 0.70–0.90 (6H,m), 0.98–1.55 (9H, m), 1.65–1.95 (5H,m), 2.05–2.25 (2H,m), 2.69–3.38 (5H, m), 3.52–4.02 (6H,m), 4.52–4.65 (1H,m), 8.07 (1H,t,J= 8Hz), 8.27 (1H,s), 8.54 (1H,s) Mass (SIMS) 412 (M⁺+1) HPLC Retention Time: 21.8 minutes

EXAMPLE 13

Synthesis of (1-(N-(3-(4-piperidyl)propanoyl)-L-tryptophyl)-4-piperidyloxy)acetic acid TFA salt (Compound (28))

In the same manner as in Example 1, 138 mg of compound (28) was produced as a white powder.
¹H-NMR (DMSO-d₆,δ): 0.78–1.45 (8H,m), 1.51–1.80 (4H, m), 2.04–2.18 (2H,m), 2.63–3.30 (8H,m), 3.38–3.62 (2H, m), 3.69–3.73 (1H,m), 3.97 (2H,d,J=8Hz), 4.95–5.08 (1H, m), 6.94–7.14 (3H,m), 7.32 (1H,d,J=7Hz), 7.54 (1H,d,J= 7Hz), 8.10–8.34 (2H,m), 8.54 (1H,s) Mass (SIMS) 485 (M⁺+1) HPLC Retention Time: 25.2 minutes

EXAMPLE 14

Synthesis of (1-(N-(3-(4-piperidyl)propanoyl)-L-seryl)-4-piperidyloxy)acetic acid TFA salt (Compound (29))

In the same manner as in Example 1, 104 mg of compound (29) was produced as a white powder.
¹H-NMR (DMSO-d₆,δ): 1.13–1.58 (8H,m), 1.68–1.94 (4H, m), 2.05–2.20 (2H,m), 2.70–2.90 (2H,m), 2.95–3.97 (9H, m), 4.01–4.12 (2H,m), 4.73–4.85 (1H,m), 7.95–8.10 (1H, m), 8.12–8.38 (1H,m), 8.46–8.65 (1H,m) Mass (SIMS) 386 (M⁺+1) HPLC Retention Time 5.3 minutes

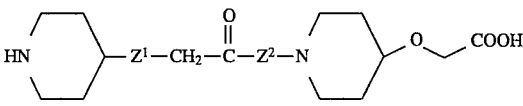

| Example | Z¹ | Z² |
|---|---|---|
| 4 | O | Tyr |
| 5 | CH₂ | Tyr |
| 6 | CH₂ | Phe |
| 7 | CH₂ | Val |
| 8 | CH₂ | Ala |
| 9 | CH₂ | Gly |
| 10 | CH₂ | Pro |
| 11 | CH₂ | Leu |
| 12 | CH₂ | Ile |
| 13 | CH₂ | Trp |
| 14 | CH₂ | Ser |

EXAMPLE 15

Synthesis of 3-(1-(N-(3-(4-piperidyl)propanoyl)-O-methyl-L-tyrosyl)-4-piperidyl)propanoic acid TFA salt (Compound (35))

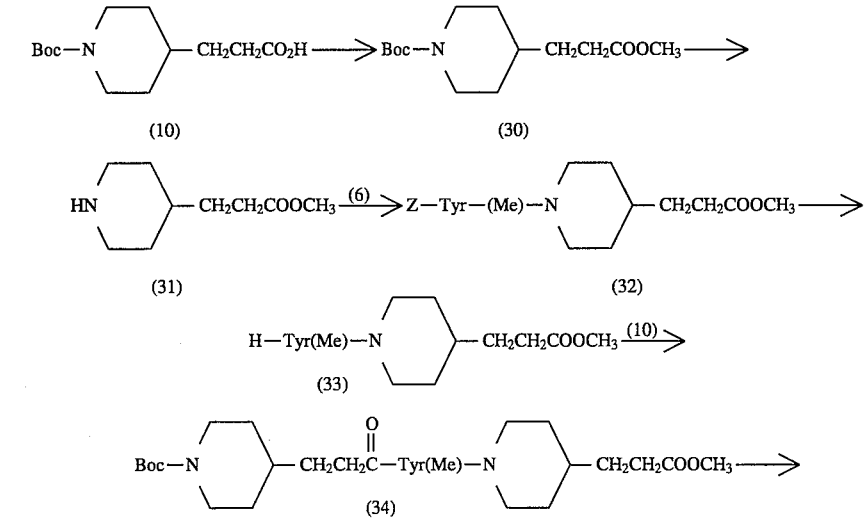

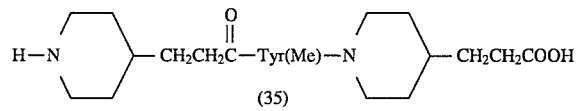

① Synthesis of Methyl 3-(1-(T-butyloxycarbonyl-4-piperidyl) propanoate (Compound (30))

14 mg of 4-dimethylaminopyridine and 0.5 ml of methanol were added to a methylene chloride (5 ml) solution of 300 mg of compound (10) that had been obtained in Example 1-④, and 269 mg of WSC·HCl was added at 5° C. and these stirred at 5° C. for 2 hours and then overnight at room temperature. Next, this was treated in the same manner as in Example 1-② to obtain 300 mg of compound (30).

② Synthesis of Compound (32)

An acetonitrile (1.5 ml) solution of 542 mg of methanesulfonic acid was added to an acetonitrile (2 ml) solution of 306 mg of compound (30) and stirred at room temperature for 30 minutes. 4 ml of DMF and 786 μl of triethylamine were added at 5° C. Next, 409 mg of compound (6) and 208 mg of HOBT·H₂O were added and dissolved. Then, 261 mg of WSC·HCl was added and stirred at 5° C. for 30 minutes and then at room temperature overnight. Next, this was treated in the same manner as in Example 1-② to obtain 590 mg of compound (32).

③ Synthesis of Compound (33)

400 mg of 10% Pd/C (50% wet) was added to an ethanol (10 ml) solution of 590 mg of compound (32) and stirred in a hydrogen atmosphere at room temperature for 1.5 hours. The catalyst was removed by filtration, and the solvent was removed by distillation under a reduced pressure. Thus, 386 mg of compound (33) was obtained as an oil.

④ Synthesis of Compound (34)

To a DMF (5 ml) solution of 193 mg of compound (33) were added 73 μl of triethylamine, 147 mg of compound (10) and 96 mg of HOBT·H₂O , and 120 mg of WSC·HCl was added at 5° C. and stirred for 30 minutes at 5° C. and then overnight at room temperature. This was treated in the same manner as in Example 1-⑤ to give 452 mg of compound (34) as an oil.

$^1$H-NMR (CDCl$_3$,δ): 0.8–1.74 (14 H,m), 1.45 (9 H,s), 2.15–3.04 (10H,m), 3.67 (3H,s), 3.77 (3H,s), 3.60–3.81 (2H,m), 4.00–4.17 (2H,m), 4.53 (1H,d,J=13Hz), 5.08–5.20 (1H,m), 6.75–6.86 (2H,m), 6.99–7.13 (2H,m)

⑤ Synthesis of Compound (35)

50 mg of lithium hydroxide was added to a methanol (1 ml)-THF (1 ml)-water (1 ml) solution of 452 mg of compound (34) and stirred for 1 hour at room temperature. This was made to have pH 1 with 1N HCl, and then extracted three times with ethyl acetate, and the organic layer was washed with brine. This was dried with magnesium sulfate, and the solvent was removed by distillation under reduced pressure. Thus, 369 mg of the corresponding carboxylic acid was obtained as a white solid. Next, this was left in TFA (5 ml) at room temperature for 30 minutes, the TFA was removed by distillation under reduced pressure, and the residue was purified by HPLC to give 285 mg of compound (35) as an oil.

$^1$H-NMR (DMSO-d$_6$,δ): 0.15–1.05 (2H,m), 1.08–1.80 (12H, m), 2.00–2.27 (4H,m), 2.60–2.91 (5H,m), 3.16–3.28 (2H, m), 3.70 (3H,s), 3.81–3.92 (2H,m), 4.27–4.39 (1H,m), 4.81–4.94 (1H,m), 6.78–6.85 (2H,m), 7.12 (2H,d,J=9Hz), 8.15 (1H,s), 8.21 (2H,d,J=9Hz), 8.48 (1H,s) Mass (SIMS) 474 (M$^+$+1) HPLC Retention Time: 27.7 minutes

EXAMPLE 16

Synthesis of 3-(1-(N-(4-piperidyloxyacetyl)-O-methyl-L-tyrosyl-4-piperidyl)propanoic acid TFA salt (Compound (37))

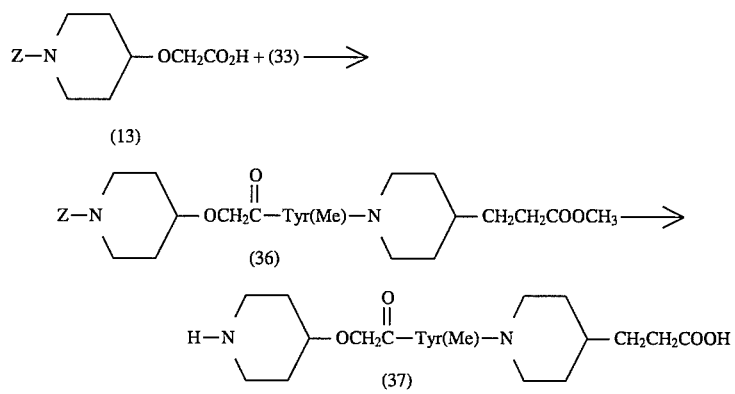

① Synthesis of Compound (36)

To a DMF (5 ml) solution of 193 mg of compound (33) were added 73 μl of triethylamine, 168 mg of compound (13) and 96 mg of HOBT·H₂O, and 120 mg of WSC·HCl was added thereto at 5° C. and stirred for 30 minutes at 5° C. and then overnight at room temperature. Next, this was treated in the same manner as in Example 1-⑤ to obtain 327 mg of compound (36) as an oil.

$^1$H-NMR (CDCl$_3$,δ): 0.80–1.20 (2H,m), 1.33–1.95 (6H,m), 2.20–2.55 (4H,m), 2.84–3.03 (3H,m), 3.15–3.30 (3H,m), 3.45–4.00 (5H,m), 3.67 (3H,s), 3.76 (3H,s), 4.50–4.60 (1H, m), 5.13 (2H,s), 5.08–5.22 (1H,m), 6.74–6.85 (2H,m), 7.00–7.15 (2H,m), 7.36 (5H,s)

② Synthesis of Compound (37)

50 mg of lithium hydroxide was added to a methanol (1 ml)-TFH (1 ml)-water (1 ml) solution of 327 mg of compound (36) and stirred for 1 hour at room temperature. This was made to have pH 1 with 1N HCl, and then extracted three times with ethyl acetate, and the organic layer was washed with brine. This was dried with magnesium sulfate, and the solvent was removed by distillation under reduced pressure. Thus, 314 mg of the corresponding carboxylic acid was obtained as a white solid. Next, this was dissolved in 10 ml of ethanol, and 200 mg of 10% Pd/C (50% wet) was added and stirred in a hydrogen atmosphere for 1.5 hours at room temperature. The catalyst was removed by filtration, and the solvent was removed by distillation under reduced pressure. Then, the residue was purified by HPLC to give 183 mg of compound (37) as an oil.

$^1$H-NMR (DMSO-$d_6$,$\delta$): 0.28–1.05 (2H,m), 1.38–2.00 (8H, m), 2.10–2.30 (2H,m), 2.70–3.30 (6H,m), 3.49–3.60 (1H, m), 3.71 (3H,s), 3.79–3.96 (2H,m), 4.25–4.39 (1H,m), 4.91–5.00 (1H,m), 6.77–6.90 (2H,m), 7.04–7.18 (2H,m), 7.82 (1H,t,J=10Hz), 8.46 (2H,s) Mass (SIMS) 476 (M$^+$+1) HPLC Retention Time: 27.5 minutes

EXAMPLE 17

Synthesis of
3-(1-(N-(3-(4-piperidyl)propanoyl)-L-tyrosyl)-
4-piperidyl)propanoic acid TFA salt
(Compound (42))

③ Synthesis of Compound (41)

To a DMF (5 ml) solution of 176 mg of compound (40) were added 63 μl of triethylamine, 128 mg of compound (10) and 84 mg of HOBT·H$_2$O, and 105 mg of WSC·HCl was added at 5° C. and stirred for 30 minutes at 5° C. and then overnight at room temperature. This was treated in the same manner as in Example 1-⑤ to obtain 274 mg of compound (41) as an oil.

$^1$H-NMR (CDCl$_3$,$\delta$): 0.82–1.76 (14H,m), 1.32 (9H,s), 1.45 (9H,s), 2.14–3.08 (10H,m), 3.66 (3H,s), 3.48–3.80 (2H,m), 3.98–4.19 (2H,m), 4.52 (1H,d,J=13Hz), 5.05–5.22 (1H,m), 6.87–6.98 (2H,m), 7.03–7.16 (2H,m)

④ Synthesis of Compound (42)

50 mg of lithium hydroxide was added to a methanol (3 ml)-THF (3 ml)-water (3 ml) solution of 274 mg of compound (41) and stirred for 1 hour at room temperature. This was made to have pH 1 with 1N HCl, and then extracted three times with ethyl acetate, and the organic layer was washed with brine. This was dried with magnesium sulfate, and the solvent was removed by distillation under reduced pressure. Thus, 260 mg of the corresponding carboxylic acid was obtained as a white solid. Next, this was left in TFA (10 ml)-anisole (1 ml) at room temperature for 30 minutes, then the TFA was removed by distillation under a reduced pressure, and the residue was purified by HPLC to give 122 mg of compound (42) as a white powder.

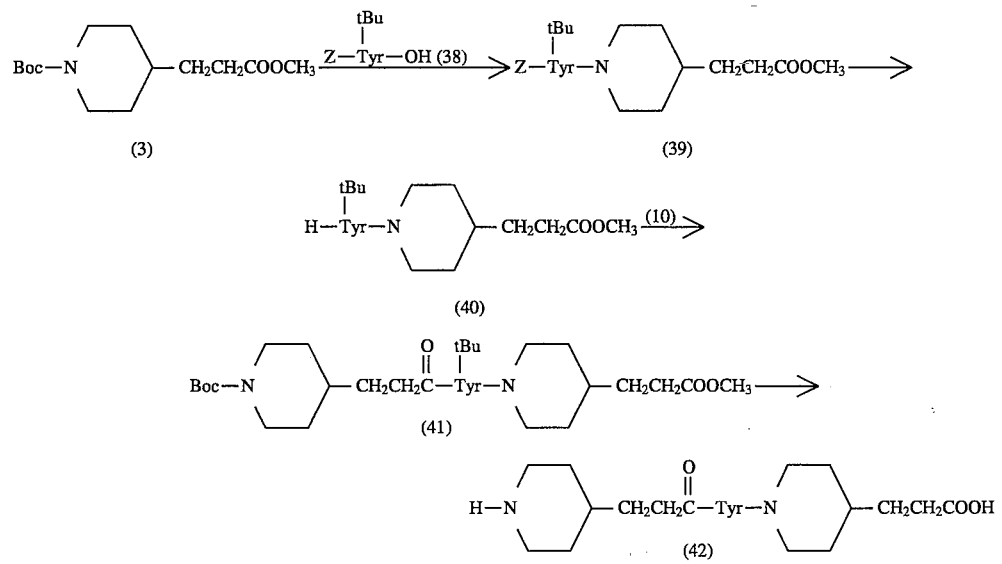

① Synthesis of Compound (39)

An acetonitrile (1.5 ml) solution of 501 mg of methanesulfonic acid was added to an acetonitrile (2 ml) solution of 283 mg of compound (30) and stirred for 30 minutes at room temperature. To this were added 4 ml of DMF and 726 μl of triethylamine at 5° C. Next, 387 mg of compound (38) and 192 mg of HOBT·H$_2$O were added and dissolved. Then, 241 mg of WSC·HCl was added and stirred at 5° C. for 30 minutes and then overnight at room temperature. Next, this was treated in the same manner as in Example 1-② to obtain 528 mg of compound (39).

② Synthesis of Compound (40)

400 mg of 10% Pd/C (50% wet) was added to an ethanol (10 ml) solution of 528 mg of compound (39) and stirred in a hydrogen atmosphere at room temperature for 1.5 hours. Then, the catalyst was removed by filtration, and the solvent was removed by distillation under a reduced pressure. Thus, 353 mg of compound (40) was obtained as an oil.

$^1$H-NMR (DMSO-$d_6$,$\delta$): 0.39–1.02 (2H,m), 1.08–1.80 (9H, m), 2.00–2.29 (4H,m), 2.37–2.93 (7H,m), 3.15–3.60 (8H, m), 3.80 (1H,d-like,J=11Hz), 4.33 (1H,d-like,J=12Hz), 4.79–4.91 (1H,m), 6.58–6.70 (2H,m), 6.98 (2H,d,J=9Hz), 8.19 (2H,d,J=9Hz), 8.51 (1H,s), 9.23 (1H,s) Mass (SIMS) 460 (M$^+$+1) HPLC Retention Time: 21.4 minutes

EXAMPLE 18

Synthesis of
3-(1-(N-(4-piperidyloxyacetyl)-L-tyrosyl)-
4-piperidyl)propanoic acid TFA salt
(Compound (44))

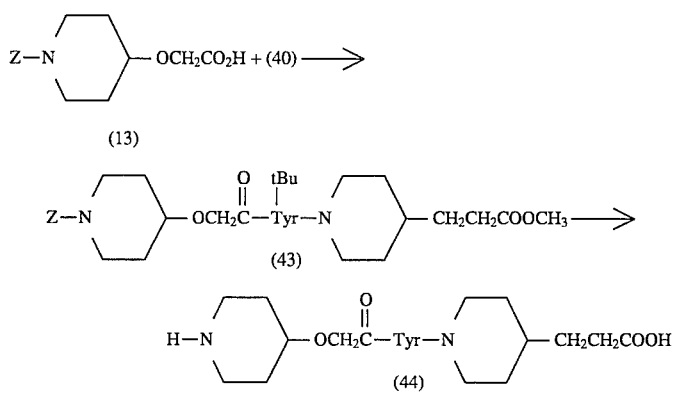

① Synthesis of Compound (43)

To a DMF (5 ml) solution of 176 mg of compound (40) were added 63 μl of triethylamine, 146 mg of compound (13) and 84 mg of HOBT·H₂O, and 105 mg of WSC·HCl was added at 5° C. and stirred for 30 minutes at 5° C. and then overnight at room temperature. This was treated in the same manner as in Example 1-⑤ to obtain 284 mg of compound (43) as a white powder.

$^1$H-NMR (CDCl$_3$,δ): 0.85–1.15 (2H,m), 1.32 (9H,s), 1.42–1.95 (6H,m), 2.24–2.32 (2H,m), 2.83–3.07 (3H,m), 3.17–3.31 (3H,m), 3.49–3.64 (2H,m), 3.66 (3H,s), 3.70–3.90 (4H,m), 3.91–4.01 (2H,m), 4.47–4.59 (1H,m), 5.13 (2H,s), 5.05–5.20 (1H,m), 6.90 (2H,d,J=9Hz), 7.06 (2H,d,J=9Hz), 7.36 (5H,s)

② Synthesis of Compound (44)

50 mg of lithium hydroxide was added to a methanol (3 ml)-THF (3 ml)-water (3 ml) solution of 284 mg of compound (43) and stirred for 1 hour at room temperature. This was made to have pH 1 with 1N HCl, and then extracted with ethyl acetate (three times), and the organic layer was washed with brine. This was dried with magnesium sulfate, and the solvent was removed by distillation under reduced pressure. Thus, 280 mg of the corresponding carboxylic acid was obtained as a white solid. This was dissolved in 10 ml of ethanol, and 200 mg of 10% Pd/C (50% wet) was added and stirred in a hydrogen atmosphere for 1.5 hours at room temperature. The catalyst was removed by filtration, and the solvent was removed by distillation under reduced pressure. Then, TFA (10 ml) and anisole (1 ml) were added to this and left at room temperature for 30 minutes. The TFA was removed by distillation under a reduced pressure, and the residue was purified by HPLC to give 165 mg of compound (44) as a white solid.

$^1$H-NMR (DMSO-d$_6$,δ): 0.37–1.08 (2H,m), 1.28–1.98 (9H, s), 2.14–2.28 (2H,m), 2.67–3.27 (7H,m), 3.50–3.60 (1H,m), 3.75–4.05 (5H,m), 3.89 (2H,s), 4.32 (1H,d-like,J=13Hz), 4.87–4.99 (1H,m), 6.60–6.70 (2H,m), 6.90–7.04 (2H,m), 7.78 (1H,t,J=7Hz), 8.44 (2H,s) Mass (SIMS) 462 (M$^+$+1) HPLC Retention Time: 22.1 minutes

EXAMPLE 19

Platelet Aggregation Inhibiting Effect

Blood was collected from the elbow vein of a healthy man, to which was added 3.8% sodium citrate of ¹⁄₁₀ times by volume the blood. This was centrifuged at 1000 rpm (150 g) for 10 minutes, and the resulting supernatant of a platelet-rich plasma (PRP) was collected. 2 μl of a solution of a test compound was added to 200 μl of the PRP and kept at 37° C. for 2 minutes while stirring at 1000 rpm. Then, 22 μl of a platelet aggregation promoter of ADP (adenosine diphosphate, final concentration: 3 μg/ml) was added. The degree of platelet aggregation of the sample was measured by colorimetry, using a hematracer (ex Niko Bioscience Co.). The platelet aggregation inhibiting activity of the test compound was represented by IC$_{50}$, which indicates the concentration of the compound that was needed to inhibit the platelet aggregation by 50%. The results are shown below.

| Test Compound | IC$_{50}$ (nM) |
|---|---|
| Compound (12) | 60 |
| Compound (15) | 48 |
| Compound (18) | 680 |
| Compound (19) | 61 |
| Compound (20) | 135 |
| Compound (21) | 917 |
| Compound (22) | 1100 |
| Compound (23) | 389 |
| Compound (24) | 2380 |
| Compound (25) | 316 |
| Compound (26) | 929 |
| Compound (27) | 507 |
| Compound (28) | 438 |
| Compound (29) | 886 |
| Compound (35) | 712 |
| Compound (37) | 117 |
| Compound (42) | 1730 |
| Compound (44) | 630 |

EXAMPLE 20

Bonding of Platelets to Fibrinogen, Fibronectin or Collagen 50 ng/ml of PGI$_2$ was added to the PRP sample and subjected to centrifugation at 11000 rpm for 2 minutes, by which the platelets were precipitated. The platelet precipitate was washed with 3.8 mM Hepes buffer (pH 7.4, Tyrode-Hepes buffer) containing 0.14 M NaCl, 2.7 mM KCl, 3.7 mM NaH$_2$PO$_{4, 0.98}$ mM MgCl$_2$, 1 mg/ml of glucose, 50 ng/ml of PGI$_2$ and 0.35% BSA. 5 μM epinephrine and 30 μM ADP were added in this order and left at room temperature for 5 minutes, by which the platelets were activated. These were then transferred into a 0.05% paraformaldehyde solution and left at room temperature for 30 minutes, whereby the platelets were fixed in the solution. The thus-fixed platelets were suspended in the Hepes buffer at a concentration of 2×10$^8$ ml$^{-1}$.

Fibrinogen (ex Kabi Co.), fibronectin (ex Sigma Co.) or collagen (ex Horm Co.) was diluted with 0.1 M NaHCO$_3$ to have a concentration of 5 μg/ml, put into each well of a 96-well microplate (ex Nunc Co.) at 200 μl/well and left at 4° C. overnight. Then, the plate was washed with a phosphate buffered saline (PBS) and blocked with 3% BSA at 37° C. for 1 hour. To the plate were added the platelet suspension (final concentration: $10^8$ ml$^{-1}$) and a varying concentration of a test compound (total amount: 200 μl/well), and the plate was kept at 37° C. for 2 hours. Then, this was washed with PBS, and 2 μg/ml of an anti-CD9 monoclonal antibody was added and kept at 37° C. for 60 minutes. Next, this was treated with a 1/1000 dilution of an enzyme (HRP)-labeled anti-mouse IgG polyclonal antibody at 37 °C. for 60 minutes, and 100 μl/well of an HRP-coloration substrate (0.1 M phosphate buffer with pH 5, containing 0.4 mg/ml of o-phenylenediamine, 0.01% H$_2$O$_2$ and 0.1 M citric acid) was added and reacted at room temperature for 15 minutes. By adding 20 μl/well of 4.5 M H$_2$SO$_4$, the reaction was stopped. Then, the absorbance of the thus-reacted sample at 490 nm was measured. The effect of the test compound was represented by IC$_{50}$, which indicates the concentration of the compound that was needed to inhibit the bonding of platelets to fibrinogen, fibronectin or collagen by 50%. The results are shown below.

| Test Compound | Fibrinogen (μM) | Fibronectin (μM) | Collagen (μM) |
|---|---|---|---|
| Compound (12) | 0.45 | 67 | >100 |
| Compound (15) | 0.25 | 0.24 | >100 |
| Compound (18) | 63 | 7.2 | >100 |

We claim:

1. A compound represented by formula

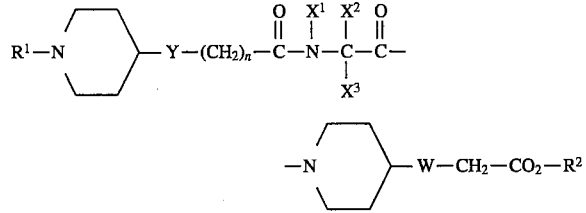

wherein R$^1$ represents a hydrogen atom or a lower alkyl group; Y represents a single bond or an oxygen atom; n represents 1, 2 or 3; W represents a methylene group or an oxygen atom; R$^2$ represents a hydrogen atom or a carboxyl modifying group which can be eliminated in vivo; X$^1$ and X$^3$ are the same or different and each represents a hydrogen atom or a lower alkyl group;

X$^2$ represents a hydrogen atom, a lower alkyl group, an aryl group, —CHX$^4$OX$^5$ (wherein X$^4$ represents a hydrogen atom or a methyl group; X$^5$ represents a hydrogen atom or a hydroxyl modifying group), —CH$_2$CH$_2$OX$^5$ (wherein X$^5$ represents the same meaning as above), —CX$^4{}_2$SX$^6$ (wherein X$^4$ represents the same meaning as above; X$^6$ represents a hydrogen atom or a thiol modifying group), —CH$_2$CH$_2$S(O)$_m$CH$_3$ (wherein m represents 0, 1 or 2), —(CH$_2$)$_p$COOX$^7$ (wherein p represents 1 or 2; X$^7$ represents a hydrogen atom or a carboxyl modifying group), —(CH$_2$)$_p$CONHX$^8$ (wherein p represents the same meaning as above; X$^8$ represents a hydrogen atom or an amide modifying group) —(CH$_2$)$_q$NHX$^9$ (wherein q represents 3 or 4; X$^9$ represents a hydrogen atom or an amino modifying group), —(CH$_2$)$_q$NHC(=NH)NHX$^{10}$ (wherein q represents the same meaning as above; X$^{10}$ represents a hydrogen atom or a guanidino modifying group), or —(CH$_2$)$_r$X$^{11}$ (wherein X$^{11}$ represents a halogen atom, a cycloalkyl group, an aryl group, a substituted aryl group, a heterocyclic group or a substituted heterocyclic group; r represents 1 or 2); provided that X$^1$ and X$^2$ may be combined together to form a trimethylene or tetramethylene group, or X$^2$ and X$^3$ may be combined together to form a pentamethylene group; or a pharmaceutically acceptable salt thereof.

2. A compound according to claim 1, wherein X$^1$ is a hydrogen atom or a lower alkyl group, X$^2$ is a hydrogen atom, a lower alkyl group, —CHX$^4$OX$^5$ (wherein X$^4$ and X$^5$ represent the same meanings as above) or —(CH$_2$)$_r$X$^{11}$ (wherein X$^{11}$ and r represent the same meanings as above), or X$^1$ and X$^2$ are combined together to form a trimethylene or tetramethylene group.

3. A compound according to claim 1, wherein Y is an oxygen atom and n is 1, or Y is a single bond and n is 2.

4. A compound according to claim 3, wherein Y is an oxygen atom and n is 1, or Y is a single bond and n is 2.

5. A compound according to any one of claims 1–4, wherein R$^1$ is a hydrogen atom.

6. A pharmaceutical composition for inhibiting platelet aggregation or bone resorption comprising an effective amount of a compound according to any one of claims 1–4, and a pharmaceutically acceptable carrier.

7. A pharmaceutical composition for inhibiting platelet aggregation or bone resorption comprising an effective amount of a compound according to claim 5, and a pharmaceutically acceptable carrier.

8. A method for inhibiting platelet aggregation by administering to a human or an animal an effective amount of a compound according to any one of claims 1–4.

9. A method for inhibiting platelet aggregation by administering to a human or an animal an effective amount of a compound according to claim 5.

10. A method for inhibiting bone resorption by administering to a human or an animal an effective amount of a compound according to any one of claims 1–4.

11. A method for inhibiting bone resorption by administering to a human or an animal an effective amount of a compound according to claim 5.

* * * * *